United States Patent [19]

Berman et al.

[11] Patent Number: 4,895,755

[45] Date of Patent: Jan. 23, 1990

[54] HALOGENATED ADVANCED EPOXY RESINS

[75] Inventors: Jody R. Berman; Chun S. Wang, both of Lake Jackson; Louis L. Walker, Clute, all of Tex.; Abel Mendoza, Midland, Mich.

[73] Assignee: The Dow Chemical Company, Midland, Mich.

[21] Appl. No.: 259,449

[22] Filed: Oct. 14, 1988

Related U.S. Application Data

[63] Continuation of Ser. No. 126,398, Nov. 30, 1987, abandoned, which is a continuation-in-part of Ser. No. 907,706, Sep. 15, 1986, Pat. No. 4,727,119.

[51] Int. Cl.$^4$ .............................................. C08G 59/02
[52] U.S. Cl. ...................................... 428/290; 428/416; 428/418; 525/481; 525/482; 525/484; 525/527; 528/98; 528/102
[58] Field of Search ..................... 428/290, 416, 418; 525/481, 482, 484, 527; 528/98, 102

[56] References Cited

U.S. PATENT DOCUMENTS

| | | | |
|---|---|---|---|
| 3,004,951 | 10/1961 | Dazzi | 528/102 |
| 3,058,946 | 10/1962 | Nametz | 528/102 X |
| 3,294,742 | 12/1966 | Bremmer | 260/47 |
| 3,929,908 | 12/1975 | Orlando et al. | 528/102 X |
| 3,956,403 | 5/1976 | Orlando et al. | 528/102 |
| 3,974,235 | 8/1976 | Cooper et al. | 528/102 |
| 3,989,531 | 11/1976 | Orlando et al. | 528/102 |
| 4,058,570 | 11/1977 | Kinson et al. | 528/102 |
| 4,104,257 | 8/1978 | Clarke | 528/102 |
| 4,170,711 | 10/1979 | Orlando et al. | 568/610 |
| 4,647,648 | 3/1987 | Silvis et al. | 528/102 |

FOREIGN PATENT DOCUMENTS

| | | |
|---|---|---|
| 0213592 | 3/1987 | European Pat. Off. . |
| 0214722 | 3/1987 | European Pat. Off. . |
| 1309346 | 10/1961 | France . |

*Primary Examiner*—Earl Nielsen

[57] ABSTRACT

Advanced epoxy resins are disclosed which result from the reaction of a relatively low molecular weight epoxy resin and a polyhydric phenol wherein at least one of the reactants contains at least one halogen atom which is meta with respect to a glycidyl ether group or a hydroxyl group attached to an aromatic ring. These advanced epoxy resins, when cured with a suitable curing agent, possess an improvement as compared to an advanced epoxy resin containing halogen atoms which are ortho with respect to a glycidyl ether group in at least one of thermal stability, glass transition temperature, relationship of viscosity to molecular weight and resistance to forming hydrolyzed halides in the presence of a refluxing solution of an alkali metal hydroxide.

75 Claims, No Drawings

HALOGENATED ADVANCED EPOXY RESINS

CROSS REFERENCE TO RELATED APPLICATION

This is a continuation, of application Ser. No. 126398 filed 11-30-87 now abandoned, which is a continuation-in-part and a division of application Ser. No. 907,706 filed Sept. 15, 1986, now U.S. Pat. No. 4,727,119.

BACKGROUND OF THE INVENTION

The present invention concerns advanced epoxy resins prepared by reacting an epoxy resin with a polyhydric phenolic compound wherein at least one of the reactants has a halogen atom which is meta with respect to a glycidyl ether group or a hydroxyl group.

Advanced epoxy resins containing halogen atoms are particularly useful in circuit boards or other electrical laminate applications, potting and encapsulation applications and other applications where flame retardant properties are desired. These halogen-containing advanced epoxy resins have the halogen atom in the ortho position with respect to the glycidyl ether groups. While these advanced halogen-containing epoxy resins possess the best properties to date which are particularly suitable for use in electrical laminates, potting and encapsulation applications and the like, it would be desirable if their properties were improved.

It has now been discovered that properties including one or more selected from thermal stability, glass transition temperature, melt viscosity to molecular weight relationship and resistance to forming hydrolyzed halides in the presence of a refluxing solution of an alkali metal hydroxide can be improved by employing an advanced epoxy resin wherein at least some of the halogen atoms are in the meta position with respect to a glycidyl ether group.

SUMMARY OF THE INVENTION

One aspect of the present invention pertains to a halogen-containing epoxy resin composition comprising (I) from about 5 to about 95, preferably from about 30 to about 60, percent by weight of at least one halogenated aromatic epoxy resin represented by the following formulas I or II

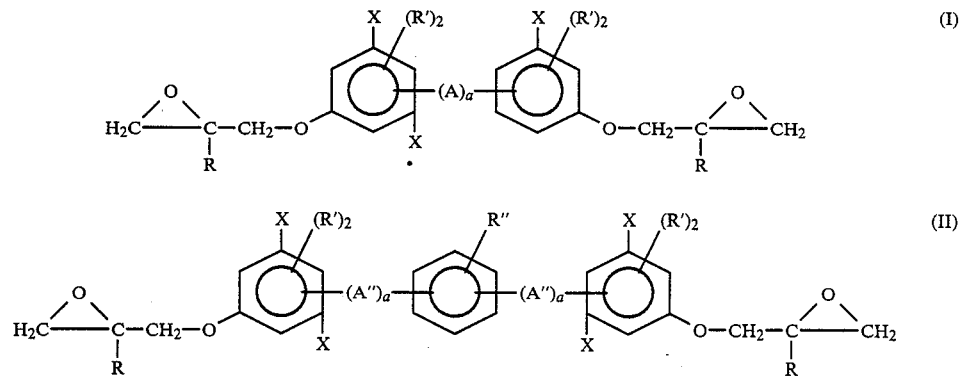

wherein each A is independently a divalent hydrocarbyl group having from 1 to about 12, preferably from 1 to about 4 carbon atoms,

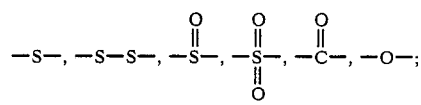

each A" independently is a divalent hydrocarbyl group having from 1 to about 4 carbon atoms; each R is independently hydrogen or an alkyl group having from 1 to about 4 carbon atoms; each R' is independently hydrogen, a hydrocarbyl or hydrocarbyloxy group having from 1 to about 10, preferably from about 1 to about 4 carbon atoms or a halogen atom, preferably chlorine or bromine; a has a value of zero or 1; each R" is independently hydrogen, a hydrocarbyl or hydrocarbyloxy group having from about 1 to about 10, preferably from about 1 to about 4, carbon atoms, a halogen atom or a glycidyl ether group; each X is independently hydrogen or a halogen atom, preferably chlorine or bromine; and wherein an average of at least 0.5, preferably an average of at least 1, most preferably an average of from about 1.5 to about 2, of the X groups for each aromatic ring is a halogen; and (II) from about 95 to about 5, preferably from about 70 to about 40 percent by weight of at least one aromatic epoxy resin represented by the following formulas III, IV, V, VI, VII, VIII, IX or X

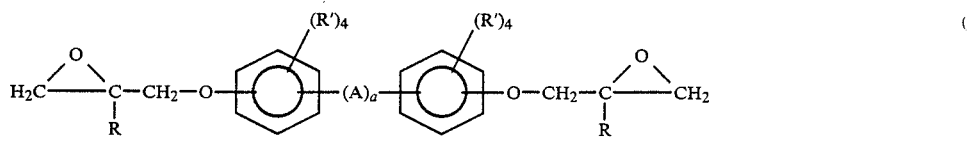

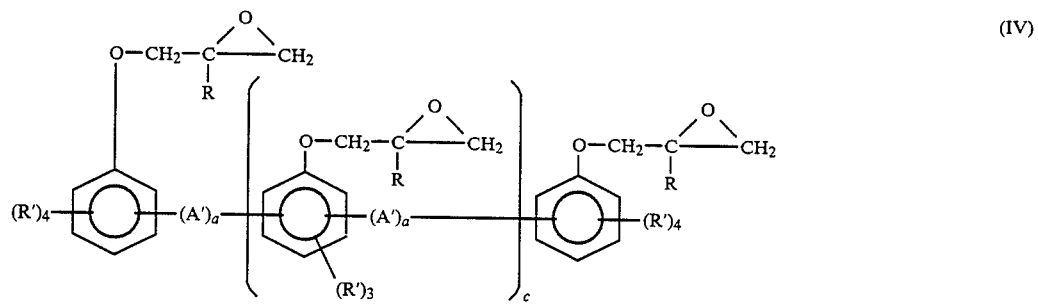
(IV)
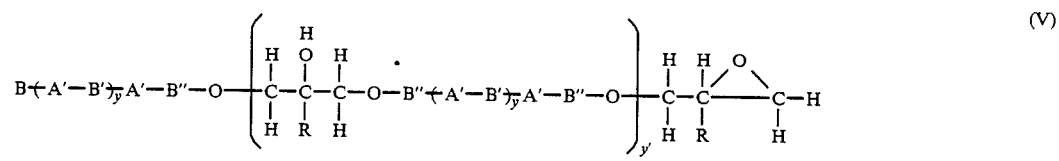
(V)
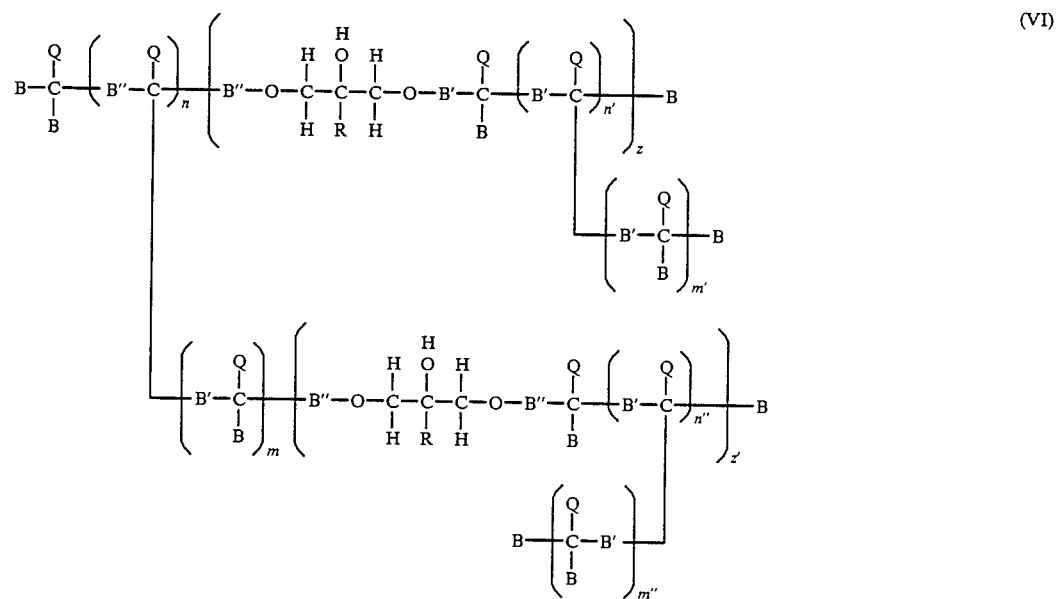
(VI)
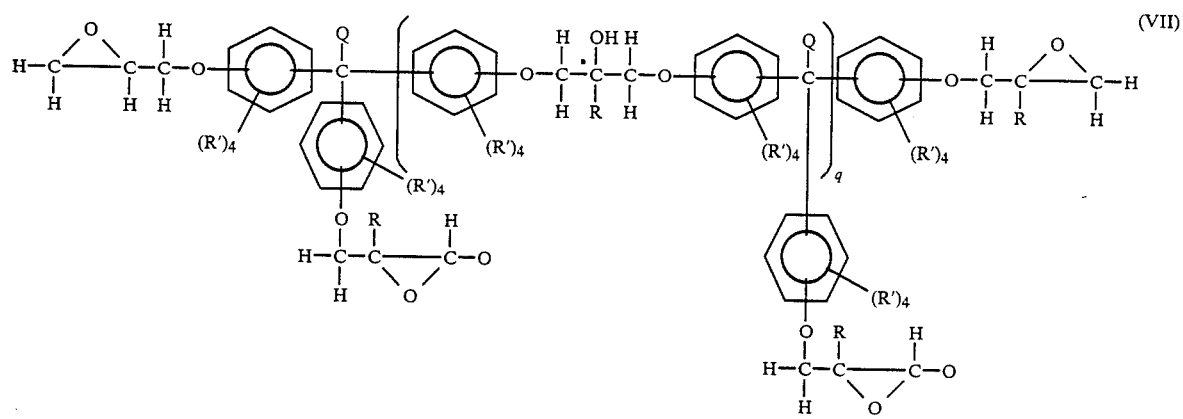
(VII)
(VIII)

-continued

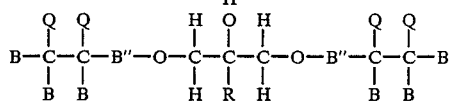
(IX)

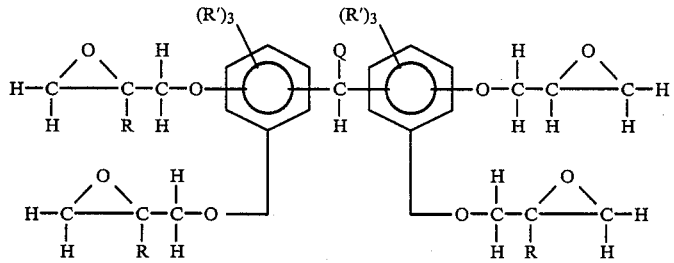
(X)

wherein A, R, R', and a are as defined above; each A' is independently a divalent hydrocarbyl group having from 1 to about 12, preferably from 1 to about 4, carbon atoms; each B is independently represented by the formula

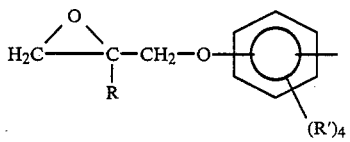

each B' is independently represented by the formula

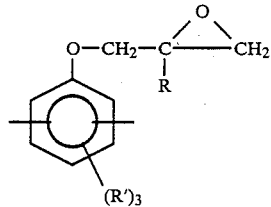

each B'' is represented by the formula

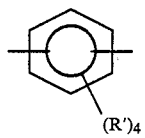

each Q is independently hydrogen or a hydrocarbyl group having from 1 to about 10 carbon atoms; m has a value of $n-1$; m' has a value of $n'-1$; m'' has a value of $n''-1$; each n, n' and n'' independently has a value from zero to about 3; q has a value from zero to about 4; each y independently has an average value from 1 to about 5; each y' independently has an average value from zero to about 3; each z and z' independently has a value of from zero to about 3; with the proviso that component II does not have any halogen atoms in the meta position with respect to a glycidyl ether group.

Another aspect of the present invention pertains to halogen-containing advanced epoxy resins which result from reacting (A) at least one epoxy resin represented by the formulas I, II, III, IV, V, VI, VII, VIII, IX or X wherein each A, A', A'', B, B', B'', Q, R, R', R'', X, a, c'', m, m', m'', n, n', n'', q, y, y', z', and z' are as defined above; and (B) at least one polyhydric phenolic compound represented by the following formulas XI, XII, XIII, XIV, XV, XVI or XVII

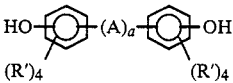
(XI)

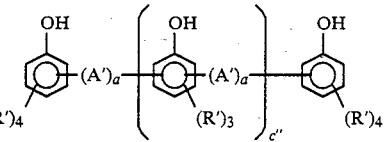
(XII)

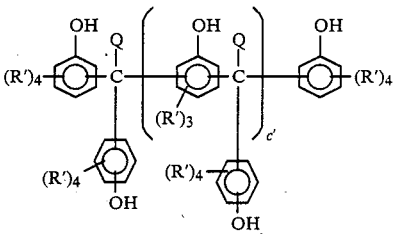
(XIII)

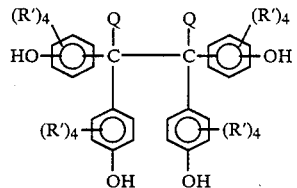
(XIV)

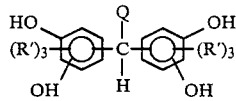
(XV)

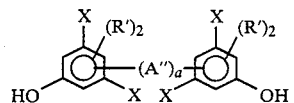
(XVI)

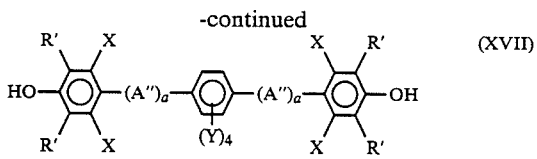

(XVII)

wherein each A, A', A", Q, R', X, and a, are as defined above; each c' and c" independently has a value from zero to about 10, preferably from about 1 to about 5; and each Y independently is hydrogen, a hydrocarbyl or hydrocarbyloxy group having from 1 to about 10, preferably from 1 to about 4 carbon atoms, a halogen atom or a hydroxyl group; and wherein (i) at least one of components (A) and (B) contains at least one halogen atom which is in the meta position with respect to an oxygen atom attached to the ring for each two aromatic rings;

(ii) when the average epoxide functionality of component (A) is not greater than 2 and the average hydroxyl functionality of component (B) is not greater than 2, components (A) and (B) are present in quantities which provide a hydroxyl to epoxide ratio of from about 0.1:1 to about 0.9:1, preferably from about 0.2:1 to about 0.7:1, most preferably from about 0.4:1 to about 0.6:1;

(iii) when one of components (A) and (B) has an average functionality of greater than 2 and the other has an average functionality of not greater than 2, components (A) and (B) are present in quantities which provide a hydroxyl to epoxide ratio of from about 0.01:1 to about 0.4:1, preferably from about 0.1:1 to about 0.3:1, most preferably from about 0.15:1 to about 0.25:1; and (iv) when both components (A) and (B) have an average functionality of greater than 2, components (A) and (B) are present in quantities which provide a hydroxyl to epoxide ratio of from about 0.01:1 to about 0.3:1, preferably from about 0.1:1 to about 0.25:1, most preferably from about 0.15:1 to about 0.2:1.

Another aspect of the present invention pertains to cured compositions resulting from curing the aforementioned halogen-containing or advanced halogen-containing epoxy resins with a curing amount of a suitable curing agent therefor.

Another aspect of the present invention pertains to a substrate impregnated with a curable composition containing the aforementioned advanced halogen-containing epoxy resins with a curing amount of a suitable curing agent therefor and an electrical or structural composite prepared from two or more layers of said impregnated substrate or a combination of said substrates.

DETAILED DESCRIPTION OF THE INVENTION

The novel halogenated relatively low molecular weight aromatic epoxy resins of the present invention represented by the formulas I and II can be prepared by dehydrohalogenating the reaction product of an epihalohydrin with a halogenated polyhydric phenolic compound wherein the halogen atoms are in the meta position with respect to a glycidyl ether group attached to an aromatic ring.

The advanced epoxy resins of the present invention are prepared by reacting the relatively low molecular weight epoxy resin with the polyhydric phenol in the presence of a catalyst and optionally in the presence of a suitable solvent system at a temperature of from about 110° C. to about 190° C. for a time sufficient to produce the desired percent epoxide.

Suitable epoxy resins which can be employed herein include, for example, the diglycidyl ethers of dihydric phenols; however, in some instances, polyglycidyl ethers of polyhydric phenols having an average functionality of from greater than about 2 to about 8 can be employed when the phenolic compound with which it is to be reacted is difunctional. Particularly suitable epoxy resins which can be employed herein include, for example, the diglycidyl ethers of bisphenols such as bisphenol A, bisphenol F, bisphenol S, biphenol, tetrabromobisphenol A, tetrabromobisphenol S, phenol-formaldehyde novolac resins, cresol-formaldehyde novolac resins, phenol-salicylaldehyde condensation products, phenol-glyoxal condensation products, combinations thereof and the like. Also suitable are the glycidyl amines of polyamine compounds such as the tetraglycidylamine of methylenedianiline and the like.

Suitable phenolic compounds which can be employed herein include, for example, the dihydric phenols; however, in some instances polyhydric phenols having an average functionality of from greater than about 2 to about 8 can be employed when the epoxy resin with which it is to be reacted is difunctional. Particularly suitable phenolic compounds which can be employed herein include, for example, bisphenols such as bisphenol A, bisphenol F, bisphenol S, biphenol, tetrabromobisphenol A, tetrabromobisphenol S, phenol-formaldehyde novolac resins, cresol-formaldehyde novolac resins, phenol-salicylaldehyde condensation products, phenol-glyoxal condensation products, combinations thereof and the like.

At least one of the reactants, i.e. the epoxy resin or the phenolic compound must contain at least one halogen atom, preferably a bromine atom, which is in the meta position with respect to the oxygen atom which is attached to the ring. Suitable halogenated epoxy resins which can be employed herein include the aforementioned epoxy resins which have been halogenated so as to contain at least one halogen atom which is in the meta position with respect to a glycidyl ether group which is attached to the ring. Suitable halogenated phenolic compounds include the aforementioned phenolic compounds which have been halogenated so as to contain at least one halogen atom which is in the meta position with respect to a hydroxyl group which is attached to the ring.

Particularly suitable halogenated epoxy resins having a halogen atom in the meta position with respect to a glycidyl ether group which can be employed herein include, for example, the diglycidyl ethers of 2,2',6,6'-tetrabromo-3,3',5,5'-tetramethyl-4,4'-biphenol; 2,2',6-tribromo-3,3',5,5'-tetramethyl-4,4'-biphenol; 1,2-bis-(2,6-dibromo-3,5-dimethyl-4-hydroxyphenyl)ethane; bis-(2,6-dibromo-3,5-dimethyl-4-hydroxyphenyl)methane, combinations thereof and the like.

Particularly suitable halogenated phenolic compounds having a halogen atom in the meta position with respect to the phenolic hydroxyl group which can be employed herein include, for example, 2,2',6,6'-tetrabromo-3,3',5,5'-tetramethyl-4,4'-biphenol; 2,2',6-tribromo-3,3',5,5'-tetramethyl-4,4'-biphenol; 1,2-bis-(2,6-dibromo-3,5-dimethyl-4-hydroxyphenyl)ethane; bis- (2,6-dibromo-3,5-dimethyl-4-hydroxyphenyl)methane, combinations thereof and the like.

The halogenated epoxy resins can be prepared by dehydrohalogenating the reaction product of an epihalohydrin and a halogenated phenolic compound with a suitable basic-acting compound such as, for example, sodium hydroxide.

Several of the halogenated dihydric phenols wherein the halogen atoms are meta with respect to the hydroxyl groups and which also have hydrocarbyl or hydrocarbyloxy groups attached to the ring can be prepared by oxidative coupling of 2,6-dimethylphenol using a palladium over carbon catalyst at a temperature of about 80° C. in the presence of oxygen gas. This product is then treated with hydrogen gas and a palladium over carbon catalyst. The resultant product is then reacted with a halogen to yield the final product. An alternative method for preparing these products is described in U.S. Pat. No. 3,956,403 and U.S. Pat. No. 4,058,570 which are incorporated herein by reference.

Those halogenated dihydric phenols wherein the halogen atoms are meta with respect to the hydroxyl groups and which do not have hydrocarbyl or hydrocarbyloxy groups attached to the ring can be prepared by, for example, dealkylation of 2,2'-dibromo-3,3',5,5'-tetra-t-butyl-4,4'-biphenol to form 2,2'-dibromo-4,4'-biphenol.

Suitable catalysts for affecting the reaction between the epoxy resin and the phenolic hydroxyl-containing compound include, for example, those disclosed in U.S. Pat. Nos. 3,306,872; 3,341,580; 3,379,684; 3,477,990; 3,547,881; 3,637,590; 3,843,605; 3,948,855; 3,956,237; 4,048,141; 4,093,650; 4,131,633; 4,132,706; 4,171,420; 4,177,216; 4,302,574; 4,320,222; 4,358,578; 4,366,295 and 4,389,520 all of which are incorporated herein by reference. Particularly suitable catalysts include, for example, those quaternary phosphonium and ammonium compounds such as, for example, ethyltriphenylphosphonium chloride, ethyltriphenylphosphonium bromide, ethyltriphenylphosphonium iodide, ethyltriphenylphosphonium acetate, ethyltriphenylphosphonium diacetate (ethyltriphenylphosphonium acetate.acetic acid complex), ethyltriphenylphosphonium tetrahaloborate, tetrabutylphosphonium chloride, tetrabutylphosphonium bromide, tetrabutylphosphonium iodide, tetrabutylphosphonium acetate, tetrabutylphosphonium diacetate (tetrabutylphosphonium acetate.acetic acid complex), tetrabutylphosphonium tetrahaloborate, tetrabromobisphenate, butyltriphenylphosphonium bisphenate, butyltriphenylphosphonium bicarbonate, benzyltrimethylammonium chloride, benzyltrimethylammonium hydroxide, benzyltrimethylammonium tetrahaloborate, tetramethylammonium hydroxide, tetrabutylammonium hydroxide, tetrabutylammonium tetrahaloborate, mixtures thereof and the like.

Other suitable catalysts include, for example, tertiary amines such as, for example, triethylamine, tripropylamine, tributylamine, 2-methylimidazole, benzyldimethylamine, mixtures thereof and the like.

Other suitable catalysts include ammonium compounds such as, for example, triethylammonium chloride, triethylammonium bromide, triethylammonium iodide, triethylammonium tetrahaloborate, tributylammonium chloride, tributylammonium bromide, tributylammonium iodide, tributylammonium tetrahaloborate, N,N'-dimethyl-1,2-diaminoethane.tetrahaloboric acid complex, mixtures thereof and the like.

Other suitable catalysts include quarternary and tertiary ammonium, phosphonium and arsonium adducts or complexes with suitable non-nucleophilic acids such as, for example, fluoboric, fluoarsenic, fluoantimonic, fluophosphoric, perchloric, perbromic, periodic, mixtures thereof and the like.

Suitable epoxy resin curing agents which can be employed herein include, for example, aromatic primary amines, aliphatic primary amines, guanadines, biguanides, sulfonamides, amides, carboxylic acids and anhydrides thereof, multifunctional phenolic hydroxyl compounds, combinations thereof and the like.

Particularly suitable epoxy resin curing agents include, for example, dicyandiamide, methylenedianiline, diaminodiphenyl sulfone, ethylene diamine, methylbicyclo[2.2.1]heptene-2,3-dicarboxylic anhydride, hexahydrophthalic anhydride, phenol-formaldehyde novolac resins, cresol-formalde-hyde novolac resins, combinations thereof and the like.

If desired, accelerators for the epoxy resins can be employed. Suitable such accelerators include the aforementioned catalysts for the reaction between the epoxy resin and the phenolic compound. Particularly suitable accelerator compounds include, for example, 2-methylimidazole, benzyl dimethyl amine, 2-ethyl-4-methylimidazole, 1-propylimidazole, ethyl triphenyl phosphonium acetate.acetic acid complex, combinations thereof and the like.

The compositions of the present invention are suitable for such applications as structural or electrical laminates or composites, coatings, adhesives, castings, moldings, electronic encapsulations and in potting compositions.

Suitable substrates which can be employed herein include, for example, fibers or filaments in woven, matt or non-woven form of glass, carbon, graphite, synthetic fibers, quartz, combinations thereof and the like.

The following examples are illustrative of the invention but are not to be construed as to limiting the scope thereof in any manner.

The glass transition (Tg) values were determined by Differential Scanning Calorimetry using a calibrated DuPont Instrument (Model No. 912 with a DuPont 1090 controller). Samples were run under a nitrogen atmosphere with a heat-up rate of 10° C. per min. (0.1667° C./sec.).

The coefficient of thermal expansion (CTES) values were determined using a calibrated DuPont Thermal Mechanical Analyzer (Model 943 with a DuPont 1090 controller).

The dynamic decomposition properties were determined using a DuPont Thermal Gravimetric Analyzer (Model No. 951 with a DuPont 1090 controller).

The dynamic mechanical properties were measured on a DuPont Dynamic Mechanical Analyzer (Model No. 982 with a DuPont 1090 controller).

The blister resistance was tested by exposing $2\frac{1}{4}'' \times 3\frac{1}{4}''$ (57.15 mm × 82.55 mm) laminate samples to 15 psig (103.4 kPa) steam in a pressure cooker for a specified amount of time. Samples were removed from the pressure cooker, dried with a paper towel, and immediately immersed in molten solder at 550° F. (260° C.) for 20 seconds. Results were recorded as the number of nonblistered sides divided by the total number of sides tested, each laminate having two sides.

The following components were employed in the Examples and Comparative Experiments.

Epoxy Resin A was the diglycidyl ether of 2,2'6-tribromo-3,3',5,5'-tetramethyl-4,4'-biphenol which had an epoxide equivalent weight (EEW) of 307 which was prepared in the following manner.

(A) Preparation of 2,2',6-tribromo-3,3',5,5'-tetramethyl-4,4'-biphenol

A 240.3 g portion of 3,3',5,5'-tetramethyldiphenoquinone was suspended in one liter of carbon tetrachloride. After cooling the slurry to 5° C. with an ice bath, 240 ml of bromine was added over a period of 10 minutes (600 s). An exothermic reaction occurred which increased the temperature to 30° C. over a period of 5 minutes (300 s). When the exotherm subsides, the mixture was brought to reflux, 65° C., and after refluxing for one hour (3600 s), the product contained 4 percent dibromo, 92 percent tribromo and 4 percent tetrabromo as determined by gas chromatography. After refluxing for one more hour (3600 s), the excess bromine was removed by distillation with the aid of one liter of fresh solvent. Once the distillate was clear, the slurry was cooled and the insoluble solid was filtered and dried. A tan solid, 446 g, was obtained which contained 4 percent dibromo, 91 percent tribromo and 5 percent tetrabromo as determined by gas chromatography. This corresponded to an 85 percent yield of the tribromo based on theoretical. The solid was washed with one liter of water and dried. It was further purified by slurrying in 1.2 l of toluene, refluxing for 15 minutes (900 s), cooling and filtering the white solid. After drying at 110° C. for 4 hours (14400 s), 285 g of white solid was obtained which contained 97 percent tribromo, 2 percent dibromo and 1 percent tetrabromo. The solid melted at 236° C.–239° C. and had the following (HNMR) spectrum: HNMR (acetone d6) delta: 2.24 (s, 3H), 2.40 (s, 9H), 6.70 (s, 1H), 7.50 (s, 1H), 7.84 (s, 1H).

(B) Preparation of Epoxy Resin

To a 5-liter reaction vessel equipped with temperature and pressure control means, a means for the continuous addition of aqueous sodium hydroxide, a means for condensing and separating water from a co-distillate mixture of water, solvent and epichlorohydrin and means for returning the solvent and epihalohydrin was added 850 g (3.8162 equiv.) of 2,2',6-tribromo-3,3',5,5'-tetramethyl-4,4'-biphenol prepared in A above, 2118 g (22.9 equiv.) of epichlorohydrin and 1412 g of the methyl ether of propylene glycol (1-methoxy-2-hydroxy propane) as a solvent. After stirring at room temperature and atmospheric pressure to thoroughly mix the contents, the temperature was raised to 55° C. and the pressure was reduced to 105 mm Hg absolute. To the resultant solution was continuously added 305.3 g (3.8162 equiv.) of 50% aqueous sodium hydroxide solution at a constant rate over a period of 3.5 hours (12600 s). During the addition of the sodium hydroxide, the water was removed by co-distilling with epichlorohydrin and solvent. The distillate was condensed thereby forming two distinct phases, an aqueous phase (top) and an organic epichlorohydrin-solvent phase (bottom). The organic phase was continuously returned to the reactor. After completion of the sodium hydroxide addition, the reaction mixture was maintained at a temperature of 55° C. and a pressure of 105 mm Hg absolute for an additional 30 minutes (1800 s). The resulting glycidyl ether was then distilled under full vacuum and a temperature up to 170° C. to remove epichlorohydrin and solvent. Part of the molten diglycidyl ether, 710 g, was dissolved in 710 g of a 75/25 by weight mixture of methyl ethyl ketone (MEK)/toluene and was maintained at a temperature of 70° C. To the resultant solution was added 2.13 g of polyethylene glycol having an average molecular weight of 400 and 4.03 g (0.0324 equiv.) of 45% aqueous potassium hydroxide. The reaction mixture was further diluted to 20% resin concentration with addition quantities of the 75/25 mixture of MEK/toluene solvent, neutralized with carbon dioxide and then washed with deionized water several times to remove salt (KCl). The organic phase from the water washes was placed on a rotary evaporator under a full vacuum and 170° C. to remove the solvent. The resultant diglycidyl ether had a Mettler softening point of 70.3° C., contained 40 percent bromine by weight and had an epoxide equivalent weight (EEW) of 307.

Epoxy Resin B was the diglycidyl ether of 2,2'6,6'-tetrabromo-3,3',5,5'-tetramethyl-4,4'-biphenol which had an EEW of 374 which was prepared in the following manner.

(A) Preparation of 2,2',6,6'-tetrabromo-3,3',5,5'-tetramethyl-4,4'-biphenol

Into a 3-necked flask were placed 24.2 g (0.1 mole) of 2,2',6,6'-tetramethyl-4,4'-biphenol and 100 ml (1.56 mole) of methylene chloride. The flask was cooled in a 20° C. water bath and 46 ml (0.9 mole) of bromine was added over a period of 5 minutes (300 s) at 25° C. The temperature of the reaction mixture was then increased to 40° C. whereupon it began to reflux and was held there for 180 minutes (10,800 s). The unreacted bromine was removed by distillation with the aid of an additional 200 ml of methylene chloride. The slurry was cooled to 25° C. and the rest of the solvent was removed in a rotary evaporator. Nuclear Magnetic Resonance (NMR) analysis of the resultant product did not detect any methyl bromination. Gas chromatography analysis indicated 4 mole percent tribromotetramethyl biphenol and 96 mole percent of tetrabromotetramethylbiphenol. Drying the solid at 110° C. for 14 hours under vacuum yielded 55.7 g of a gray solid. This solid was dispersed in 70 ml of acetone and was refluxed for 1 hour (3600 s). The slurry was then cooled and the solid was filtered and dried under a vacuum at 110° C. for 4 hours (14400 s). A white solid, 51 g, was obtained. The solid contained 98 mole percent of the desired tetra-bromo product as analyzed by gas chromatography and melted at 242°–245° C.

(B) Preparation of Epoxy Resin

To a 2-liter 5-neck round bottom flask equipped with a heating mantle, stirrer, thermometer and reflux condenser were added 300 g (1.079 equiv.) of 2,2',6,6'-tetrabromo-3,3',5,5'-tetramethyl-4,4'-biphenol prepared above, 497.3 g (5.379 moles) of epichlorohydrin, 267.78 g of isopropyl alcohol and 43.24 g of water. The temperature was raised to 65° C. and 193.55 g (0.9677 mole) of 20 percent by weight of sodium hydroxide was dripped in over a period of 45 minutes (2700 s) while maintaining the temperature at 65° C. After the addition of the sodium hydroxide, the temperature was maintained at 65° C. for an additional 15 minutes (900 s). The reaction mixture was then poured into a 2-liter separatory funnel and the aqueous phase was separated from the organic phase and discarded. The organic phase was then poured back into the reactor. The temperature was again maintained at 65° C. and 86.4 g (0.432 mole) of 20 percent by weight aqueous sodium hydroxide was dripped in over a period of 15 minutes (900 s). The temperature was maintained at 65° C. for an additional 15 minutes (900 s) following the sodium hydroxide addition. The aqueous phase was again separated and the organic phase was washed 4 times with about 500 g of deionized water. After the last washing step, the organic phase was stripped at 150° C. and 5 mm Hg for 45 minutes (2700 s). The resultant diglycidyl ether had an EEW of 374.

Epoxy Resin C was a polyglycidyl ether of a phenol-formaldehyde novolac resin which had an average functionality of 3.5 and an EEW of 180 available from The Dow Chemical Company as D.E.N. ™ 438.

Epoxy Resin D was the diglycidyl ether of bisphenol A which had an EEW of 185.9, available from The Dow Chemical Company as D.E.R. ™ 331.

Epoxy Resin E was the diglycidyl ether of bisphenol F which had an EEW of 170.1.

Epoxy Resin F was the diglycidyl ether of bisphenol S which had an EEW of 195.3.

Epoxy Resin G was the digylcidyl ether of dihydroxy benzophenone (bisphenol K) which had an EEW of 178.

Epoxy Resin H was the diglycidyl ether of biphenol which had an EEW of 165.

Epoxy Resin I was the diglycidyl ether of 3,3',5,5'-tetramethyl-4,4'-biphenol which had an EEW of 188.7.

Epoxy Resin J was the diglycidyl ether of 3,3',5,5'-tetrabromo-4,4'-biphenol which had an EEW of 349.7.

Epoxy Resin K was the diglycidyl ether of 3,3'5,5'-tetrabromo-4,4'-bisphenol-A which had an EEW of 324.7.

Epoxy Resin L was the diglycidyl ether of 3,3',5,5'-tetrabromo-4,4'-bisphenol-S which had an EEW of 341.

Epoxy Resin M was a blend of 81.8 percent by weight of a cresol epoxy novolac resin having an average functionality of 6 and an EEW of 340 and 18.2 percent by weight of a brominated epoxy resin prepared by advancing 436.7 g of Epoxy Resin K with 63.3 g of dihydric phenol A to an EEW of 450. The resultant blend had an EEW of about 356 and a bromine content of 8.83 percent by weight.

Epoxy Resin N was an advanced epoxy resin prepared by reacting Epoxy Resin D with Dihydric Phenol A at an equivalent ratio of epoxy to phenol of 2.54:1 to an EEW of 483. The advancement reaction was conducted at 160° C. for 90 min. (5400 s) in the presence of 500 ppm based on the weight of Epoxy Resin D of ethyltriphenylphosphonium acetate.acetic acid complex.

Epoxy Resin O was an advanced epoxy resin prepared by reacting Epoxy Resin D with Dihydric Phenol B at an equivalent ratio of epoxy to phenol of 2.56:1 to an EEW of 483. The advancement reaction was conducted at 160° C. for 90 min. (5400 s) in the presence of 500 ppm based on the weight of Epoxy Resin D of ethyltriphenylphosphonium acetate.acetic acid complex.

Epoxy Resin P was an advanced epoxy resin prepared be reacting Epoxy Resin D with Dihydric Phenol A at an equivalent ratio of epoxy to phenol of 2.88:1 to an EEW of 430. The advancement reaction was conducted at 160° C. for 90 min. (5400 s) in the presence of 500 ppm based on the weight of Epoxy Resin D of ethyltriphenylphosphonium acetate.acetic acid complex.

Epoxy Resin Q was a cresol-formaldehyde epoxy novolac resin having an average functionality of 6 and an EEW of 200.

Dihydric Phenol A was 4,4'-isopropylidine-bis-2,6-dibromophenol. (The bromine atoms are ortho to the hydroxyl groups).

Dihydric Phenol B was 2,2',6,6'-tetrabromo-3,3',5,5'-tetramethyl-4,4'-biphen-ol. (The bromine atoms are meta to the hydroxyl groups).

Dihydric Phenol C was bis-(2,6-dibromo-3,5-dimethyl-4-hydroxyphenyl)methane. (The bromine atoms are meta to the hydroxyl groups).

Dihydric Phenol D was 1,2-bis(2,6-dibromo-3,5-dimethyl-4-hydroxyphenyl) ethane. (The bromine atoms are meta to the hydroxyl group).

EXAMPLE 1

To 410 g of a cresol epoxy novolac resin containing 946 ppm hydrolyzable chloride by weight and having an EEW of 200 dissolved in 410 g of a 75/25 by weight mixture of MEK/toluene and 82 g of 2,2',6,6'-tetrabromo-3,3',5,5'-tetramethyl-4,4'-dihydroxybiphenyl was added 1.23 g of a polyethylene glycol having an average molecular weight of 400. After heating with stirring to 80° C., 3.59 g of 45% aqueous potassium hydroxide (1.25 eq. per eq. of hydrolyzable chloride) was added all at once and the reaction mixture maintained at 80° C. for 6 hours (21,600 s). The reaction mixture was diluted to 20% solids with a 75/25 by weight mixture of MEK/toluene mixture, neutralized with carbon dioxide and then washed several times with deionized water to remove KCl. The organic phase from the washes was placed in a rotary evaporator under a full vacuum at 160° C. to remove the solvent. A yellow, solid which had a viscosity of 376 centistokes (0.000376 m2/s) at 150° C., 9.43% by weight bromine content, 15 ppm hydrolyzed chloride by weight and an EEW of 281 was obtained.

EXAMPLE 2

To 517 g of a cresol epoxy novolac resin containing 1689 ppm hydrolyzable chloride by weight and having an EEW of 200 dissolved in a 517 g of a 75/25 by weight mixture of MEK/toluene and 103.4 g of 1,2-bis-(2,6, -dibromo-3,5-dimethyl-4-hydroxyphenyl) ethane was added 1.55 g of a polyethylene glycol having an average molecular weight of 400. After heating with stirring to 85° C., 8.5 g of 45% aqueous potassium hydroxide (1.7 eq. per eq. of hydrolyzable chloride) was added all at once and the reaction mixture maintained at 80° C. for 6 hours (21,600 s). The reaction mixture was diluted to 20% solids with a 75/25 by weight mixture of MEK/toluene mixture, neutralized with carbon dioxide and then washed several times with deionized water to remove KCl. The organic phase from the washes was placed in a rotary evaporator under a full vacuum at 160° C. to remove the solvent. A yellow, solid which had a viscosity of 409 centistokes (0.000409 m2/s) at 150° C., 8.66% by weight bromine content, 28 ppm hydrolyzed chloride by weight and an EEW of 281 was obtained.

EXAMPLE 3

A mixture of 206.5 g of a cresol epoxy novolac resin having an average functionality of 6 and an EEW of 200 and 51.6 g of the diglycidyl ether of 2,2',6-tribromo-3,3',5,5'-tetramethyl-4,4'-dihydroxybiphenyl having an EEW of 307 dissolved in 1000 g of a 75/25 by weight mixture of MEK/toluene was placed in a rotary evaporator. The solvent was removed under full vacuum at 160° C. A yellow, solid product had a viscosity of 510 centistokes (0.000510 m2/s), 2 ppm hydrolyzable chloride by weight and an EEW of 235 was obtained.

EXAMPLE 4

An advanced epoxy resin was prepared by reacting Epoxy Resin D with Dihydric Phenol C at an equivalent ratio of epoxy to phenol of 2.86:1 to an EEW of 430. The advancement reaction was conducted at 160° C. for 90 min. (5400 s) in the presence of 500 ppm based on the weight of Epoxy Resin D of ethyltriphenylphosphonium acetate.acetic acid complex.

EXAMPLE 5

An advanced epoxy resin was prepared by reacting Epoxy Resin D with Dihydric Phenol D at an equivalent ratio of epoxy to phenol of 2.81:1 to an EEW of 430. The advancement reaction was conducted at 160° C. for 90 min. (5400 s) in the presence of 500 ppm based on the weight of Epoxy Resin D of ethyltriphenylphosphonium acetate.acetic acid complex.

EXAMPLE 6

An advanced epoxy resin was prepared by reacting Epoxy Resin D with Dihydric Phenol B at an equivalent ratio of epoxy to phenol of 2.76:1 to an EEW of 430. The advancement reaction was conducted at 160° C. for 90 min. (5400 s) in the presence of 500 ppm based on the weight of Epoxy Resin D of ethyltriphenylphosphonium acetate.acetic acid complex.

EXAMPLE 7

Various epoxy resins were cured with methylenedianiline at 175° C. for 1 hour (3600 s) and post cured at 195° C. for 2 hours (7200 s) by pouring the mixture of epoxy resin and curing agent into an aluminum mold fashioned from two sheets of aluminum using ⅛ in. (3.175 mm) spacers. The epoxy resin type and quantity, the amount of curing agent and the glass transition (Tg) temperature for the cured products are given in the following Table I.

TABLE I

| RUN NO. | EPOXY RESIN TYPE/g/equiv. | CURING AGENT g/equiv. | Equiv. Cur. Agent per Equiv. Epoxy | Tg °C. |
| --- | --- | --- | --- | --- |
| 1 | A/50/0.161 | 8.2/0.166 | 1.031 | 221 |
| 2 | B/50/0.137 | 6.7/0.135 | 0.985 | 225 |
| 3* | C/50/0.278 | 13.8/0.279 | 1.004 | 221** |
| 4* | D/50/0.269 | 13.3/0.269 | 1.0 | 165 |
| 5* | E/50/0.294 | 14.6/0.295 | 1.003 | 150 |
| 6* | F/50/0.256 | 12.7/0.257 | 1.004 | 190 |
| 7* | G/50/0.281 | 13.9/0.281 | 1.0 | 185 |
| 8* | H/50/0.303 | 15.0/0.303 | 1.0 | 191 |
| 9* | I/50/0.265 | 13.1/0.265 | 1.0 | 205 |
| 10* | J/50/0.143 | 7.1/0.143 | 1.0 | 210 |
| 11* | K/50/0.154 | 7.6/0.154 | 1.0 | 200 |

TABLE I-continued

| RUN NO. | EPOXY RESIN TYPE/g/equiv. | CURING AGENT g/equiv. | Equiv. Cur. Agent per Equiv. Epoxy | Tg °C. |
| --- | --- | --- | --- | --- |
| 12* | L/50/0.142 | 7.0/0.141 | 0.993 | 186 |

*Not an example of the present invention.
**This shows that a two-functional resin of the present invention has as high or higher glass transition temperature as a multifunctional epoxy novolac resin which are one of the standard multifunctional resins for high temperature applications.

EXAMPLE 8

Various epoxy resins were cured with diaminodiphenyl sulfone by mixing the epoxy resin and the curing agent at 150° C. and after pouring the curable mixture into a hot aluminum mold fashioned from two sheets of aluminum using ⅛ in. (3.175 mm) spacers and curing in an oven at 180° C. for 1 hour (3600 s) and post curing at 200° C. for 1 hour (3600 s). The epoxy resin type and quantity, the amount of curing agent and the Dynamic Decomposition Temperature for the cured products are given in the following Table II. The Dynamic Decomposition temperature was determined by heating the sample at a rate of 3° C./min. (0.05° C./s) and observing the onset of degradation, weight loss.

TABLE II

| RUN NO. | EPOXY RESIN TYPE/g/equiv. | CURING AGENT g/equiv. | Equiv. Cur. Agent per Equiv. Epoxy | Dyn. Decomp. Temp. °C. |
| --- | --- | --- | --- | --- |
| 1 | A/50/.161 | 10.2/0.165 | 1.025 | 319 |
| 2 | B/50/137 | 8.4/0.136 | 0.992 | 320 |
| 3* | K/50/154 | 9.5/0.153 | 0.994 | 279 |
| 4* | J/50/143 | 8.9/0.144 | 1.007 | 275 |
| 5* | L/50/142 | 8.8/0.142 | 1.0 | 255 |

*Not an example of the present invention.

EXAMPLE 9

Various epoxy resins were cured with methylenedianiline by mixing the epoxy resin and the curing agent at 150° C. and after pouring the curable mixture into a hot aluminum mold fashioned from two sheets of aluminum using ⅛ in. (3.175 mm) spacers and curing in an oven at 175° C. for 1 hour (3600 s) and post curing at 200° C. for 1 hour (3600 s) and finally at 230° C. for 30 minutes (1800 s). The epoxy resin type and quantity, the amount of curing agent and the flexural strength and flexural strength retention for the cured products are given in the following Table III.

TABLE III

| RUN NO. | EPOXY RESIN Type/g/Eq. | CURING AGENT g/Equiv. | FLEXURAL STRENGTH psi (kPa) 25° C. | FLEXURAL STRENGTH psi (kPa) 180° C. | FLEXURAL STRENGTH psi (kPa) 210° C. | RETENTION OF FLEX. STR., % 180° C. | 210° C. |
| --- | --- | --- | --- | --- | --- | --- | --- |
| 1 | A/150/.483 | 23.9/0.478 | 18850 (129967) | 8238 (56799) | 6785 (46781) | 44 | 36 |
| 2 | B/150/.412 | 20.4/0.408 | 13000 (89632) | 9279 (63977) | 7866 (54235) | 71 | 61 |
| 3* | C/200/1.11 | 55.0/1.1 | 19940 (137482) | 7625 (52573) | 4575 (31544) | 38 | 23 |

*Not an example of the present invention.

EXAMPLE 10

Various epoxy resins were cured with methylenedianiline by mixing the epoxy resin and the curing agent at 150° C. and after pouring the curable mixture into a hot aluminum mold fashioned from two sheets of aluminum using ⅛ in. (3.175 mm) spacers and curing in an oven at 175° C. for 1 hour (3600 s) and post curing at 200° C. for 1 hour (3600 s) and finally at 230° C. for 30 minutes (1800 s). The epoxy resin type and quantity, the amount of curing agent and the flexural modulus and flexural modulus retention for the cured products are given in the following Table IV.

tested for their thermal properties and flame resistant properties and electrical properties.

The samples were formulated so as to contain 1.75 weight percent bromine and contained in addition to the epoxy resin and curing agent given in the Table, (1) 8.5 g of a 10 percent solution of 2-methylimidazole dissolved in the curing agent, (2) 4 g of carnauba wax available from Hoechst, (3) epoxy silane Z-6040 available from Dow Corning, (4) 685 g of fused silica, (5) 10 g of antimony oxide and 4 g of carbon black. The curing agent employed was a phenolformaldehyde novolac resin having an average functionality of 6 and a phenolic hydroxyl equivalent weight of 104.5. The amount

TABLE IV

| RUN NO. | EPOXY RESIN Type/g/Eq. | CURING AGENT g/Equiv. | FLEXURAL STRENGTH psi (kPa) 25° C. | FLEXURAL STRENGTH psi (kPa) 180° C. | FLEXURAL STRENGTH psi (kPa) 210° C. | RETENTION OF FLEX. STR., % 180° C. | RETENTION OF FLEX. STR., % 210° C. |
|---|---|---|---|---|---|---|---|
| 1 | A/150/.483 | 23.9/0.478 | 457400 (3153681) | 177200 (1221759) | 118200 (814965) | 26 | 36 |
| 2 | B/150/.412 | 20.4/0.408 | 394500 (2719999) | 225300 (1553398) | 190600 (1314149) | 57 | 48 |
| 3* | C/200/ | 55.0/ | 444600 (3065428) | 136800 (943209) | — | 31 | — |

*Not an example of the present invention.

EXAMPLE 11

Various epoxy resins were formulated into an encapsulant composition and the cured samples were tested for thermal, electrical and flame retardant properties. The formulations were blended on a two roll mill at 50°, cooled to room temperature and crushed into small pieces. Each system was then cured at 170° C. for 4 hours (14400 s) and cooled to room temperature. The cured samples were then cut into 3 mm×3 mm×160 mm coupons. The coupons were subjected to 15 psig (103.422 kPa) steam at 250° C. for the time indicated. The coupons were removed from the steam chamber, wiped dry, cooled to room temperature for about 30 minutes and then weighed to determine the percent of water uptake. Other samples of the cured products were and type of epoxy resin, amount of curing agent and the cured article results are given in Table V.

TABLE V

| | SAMPLE DESIGNATION | | | |
|---|---|---|---|---|
| | A* | B | C | D |
| EPOXY RESIN, Type/g | M/201.8 | Ex. 3/185.5 Q/16.3 | Ex. 4/201.8 | Ex. 5/201.8 |
| CURING AGENT, g | 82.7 | 82.7 | 82.7 | 82.7 |
| WATER RETENTION | | | | |
| after 20 Hrs., % | 0.78 | 0.72 | 0.71 | 0.72 |
| after 40 Hrs., % | 0.87 | 0.80 | 0.78 | 0.81 |
| after 100 Hrs., % | 0.96 | 0.83 | 0.83 | 0.88 |
| Tg (DMA)[1], °C. | 219 | 191 | 182 | 215 |
| Tg (DSC)[2], °C. | 198 | 168 | 156 | 194 |
| Tg (TMA)[3], °C. | 185 | 175 | 160 | 192 |
| CTE[4] @ 100° C., ppm/°C. | 32.1 | 47.4 | 34.2 | 36 |
| CTE[4] @ 220° C., ppm/°C. | 98.2 | 113 | 94.0 | 84.8 |
| 94-VO FLAME RETARDANCE RATING, sec. | 12 | 11 | 10 | 10 |
| DIELECTRIC CONSTANT[5] | 4.03 | 3.93 | — | 3.94 |
| DIELECTRIC CONSTANT[6] | 4.67 | 4.53 | 4.51 | 4.57 |
| DISSIPATION FACTOR[5] | 0.0031 | 0.0030 | 0.0029 | 0.0026 |
| DISSIPATION FACTOR[6] | 0.0125 | 0.0118 | 0.0115 | 0.0093 |

FOOTNOTES FOR TABLE V
*Not an example of the present invention.
[1]The glass transition temperature was determined by DMA with a heat rate of 5° C./min. (0.083° C./s).
[2]The glass transition temperature was determined by DSC with a heat rate of 10° C./min. (0.167° C./s).
[3]The glass transition temperature was determined by TMA with a heat rate of 5° C./min. (0.083° C./s).
[4]CTE is coefficient of thermal expansion.
[5]Measured at 0.3 Hz before exposure to 15 psig. (103.42 kPa) steam for 132 hours (475200 s).
[6]Measured at 0.3 Hz after exposure to 15 psig. (103.42 kPa) steam for 132 hours (475200 s).

EXAMPLE 12

Epoxy Resin M was compared to the epoxy resins of Examples 3–5 to determine which exhibited superior chemical stability to 3 normal potassium hydroxide in dioxane at reflux temperatures for 30 minutes (1800 s). The data is given in Table VI in terms of ionic chloride and ionic bromide in each system. The ionic chloride and ionic bromide were measured using silver nitrate titrant and a Brinkman potentiometric titrator.

TABLE VI

| EPOXY RESIN | IONIC Cl, ppm BEFORE | IONIC Cl, ppm AFTER | IONIC Br, ppm BEFORE | IONIC Br, ppm AFTER |
|---|---|---|---|---|
| Epoxy Resin M* | <5 | 240 | <5 | 180 |

TABLE VI-continued

| EPOXY RESIN | IONIC Cl, ppm BEFORE | IONIC Cl, ppm AFTER | IONIC Br, ppm BEFORE | IONIC Br, ppm AFTER |
|---|---|---|---|---|
| Example 3 | <5 | 215 | 0 | 0 |
| Example 4 | <5 | 235 | 0 | 0 |
| Example 5 | <5 | 240 | 0 | 0 |

*Not an example of the present invention.

EXAMPLE 13

This example demonstrates that higher melt viscosities can be obtained from advanced resins of the present invention. Higher melt viscosities help minimize resin flow during the pressing stage of laminate processing. A resin of higher viscosity has more flow control than a resin of lower viscosity. The data is given in the following Table VII. The melt viscosities were measured on an I.C.I. cone and plate viscometer at 150° C.

TABLE VII

| EPOXY RESIN | MELT VISCOSITY cps | MELT VISCOSITY Pa.s |
|---|---|---|
| Epoxy Resin M* | 440 | 0.44 |
| Example 7 | 640 | 0.64 |
| Example 8 | 660 | 0.66 |

*Not an example of the present invention.

EXAMPLE 14

A laminating varnish was prepared by blending Epoxy Eesin O (3200 g, 6.705 epoxy equiv.) with 1464 g acetone, 493 g dimethylformamide, 432 g monomethyl ether of propylene glycol, 96 g (4.571 equiv.) dicyandiamide and 3.2 g 2-methylimidazole. The varnish had a gel time of 204 seconds at 171° C. and a Zahn cup viscosity of 23 seconds.

Burlington style 7628 glass cloth with an I617 finish was impregnated with the above prepared laminating varnish in a forced air vertical treater having a total length of 26 feet (7.9 m) with the first 19.5 feet (5.9 m) heated to 350° C. at a rate of 11 ft./min. (61 mm/sec.). The resin contained in the impregnated glass cloth had a gel time at 171° C. of about 70 seconds.

The resin content was 54% by weight. Eight 12 in.×12 in. (304.8 mm×304.8 mm) plies were pressed at 350° F. (176.7° C.) for 60 min. (3600 s) at a pressure of 500 psia (3447.4 kPa). The resultant laminate had a Tg of 155° C. and 100% passed the Blister Resistance test after a 2-second dip in 500° F. (260° C.) solder.

COMPARATIVE EXPERIMENT A

A laminating varnish was prepared by blending 3200 g (6.623 equiv.) of Epoxy Resin n with 1814 g acetone, 493 g dimethylformamide, 432 g monomethyl ether of dipropylene glycol, 96 g dicyandiamide and 3.2 g 2-methylimidazole. Prepreg and laminates were prepared as in Example 13 at a treater speed of 10 feet/min. (50.8 mm/sec.). The prepreg had a gel time of 90 sec. and a resin content of 41% by weight. The resultant laminate had a Tg of 120° C. and 0% passed the Blister Resistance test.

What is claimed is:
1. A halogen-containing advanced epoxy resin which results from reacting
   (A) at least one epoxy resin represented by the following formulas I, II, III, IV, V, VI, VII, VIII, IX or X; and

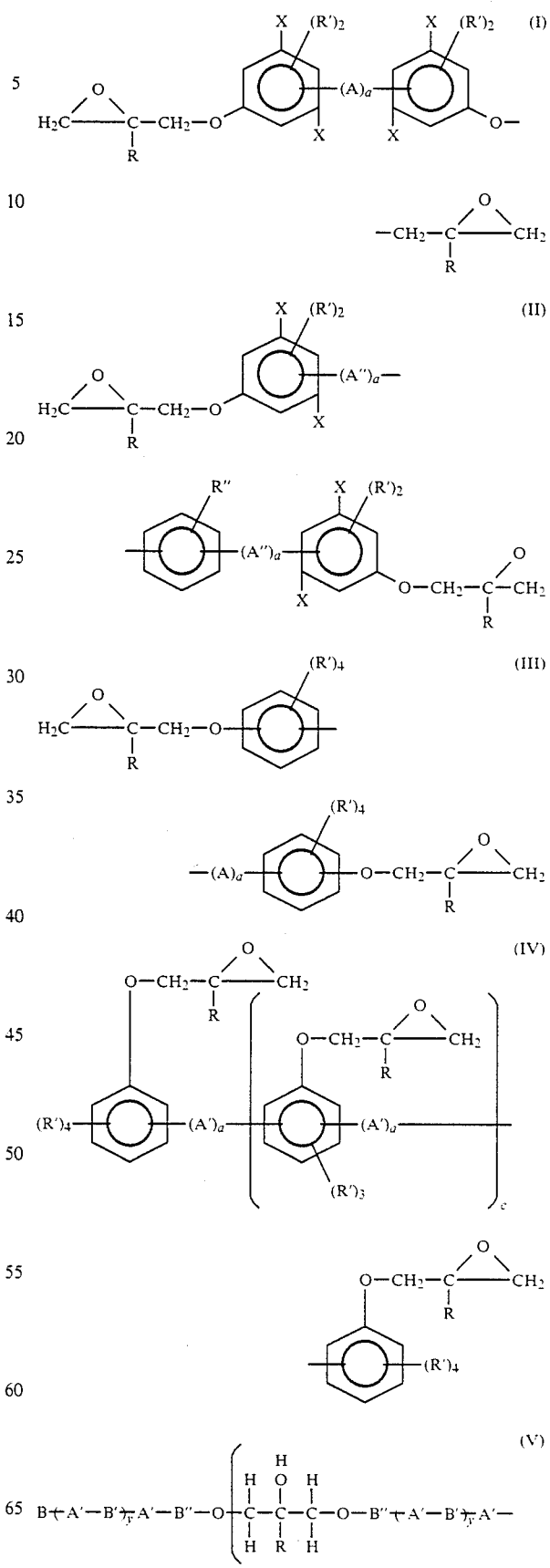

-continued
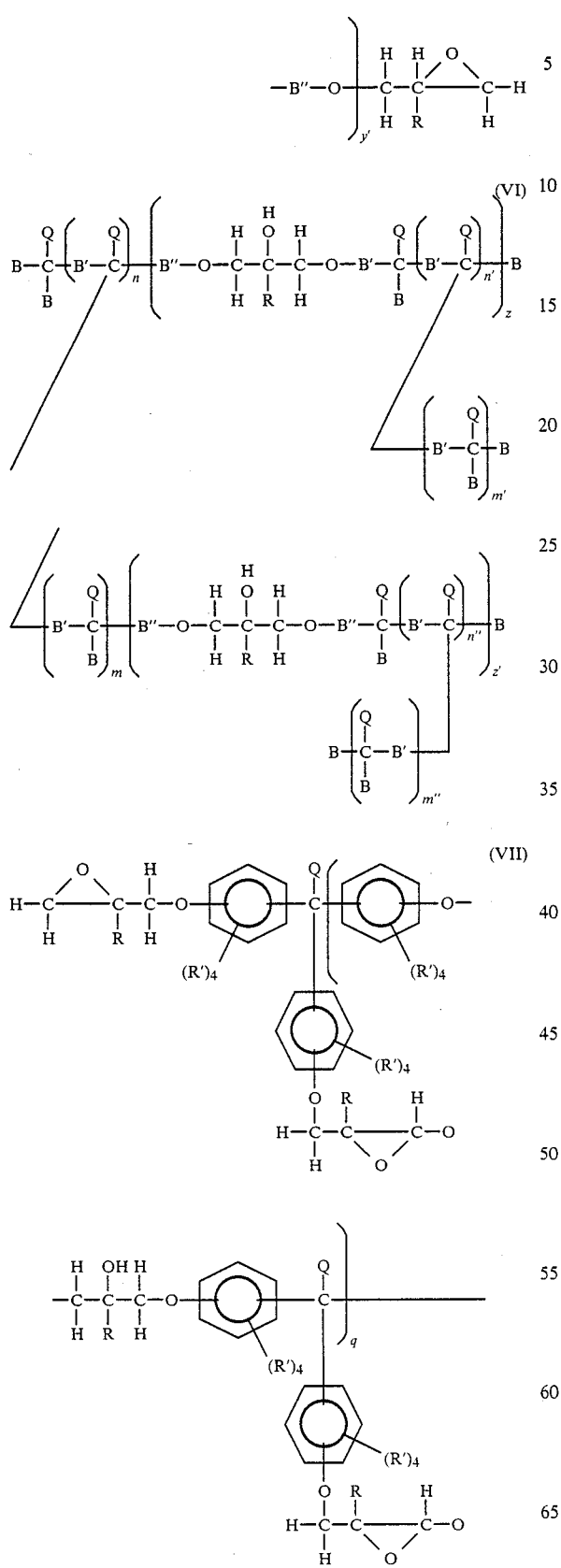
(VI)
(VII)
-continued
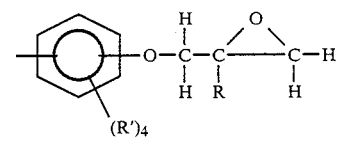
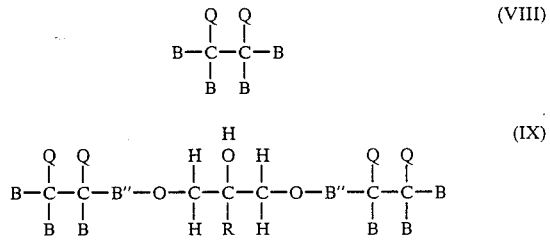
(VIII)
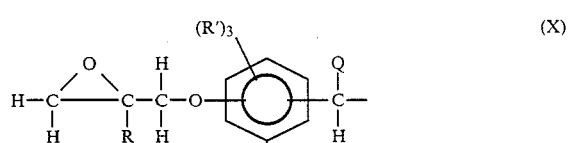
(IX)
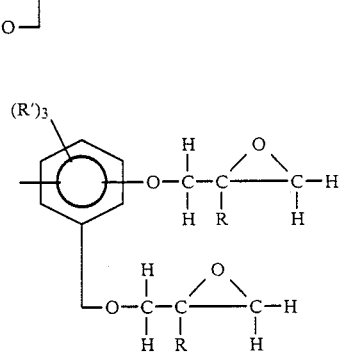
(X)
(B) at least one polyhydric phenolic compound represented by the following formulas XI, XII, XIII, XIV, XV, XVI or XVII
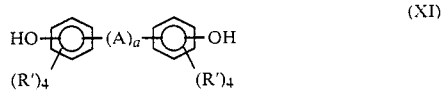
(XI)
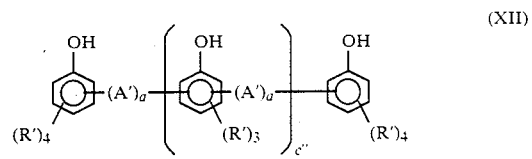
(XII)
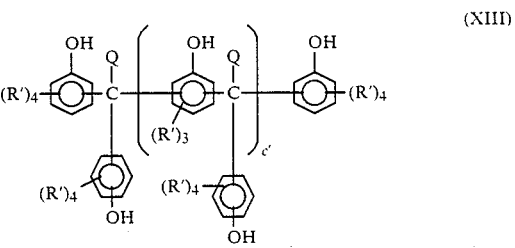
(XIII)

-continued

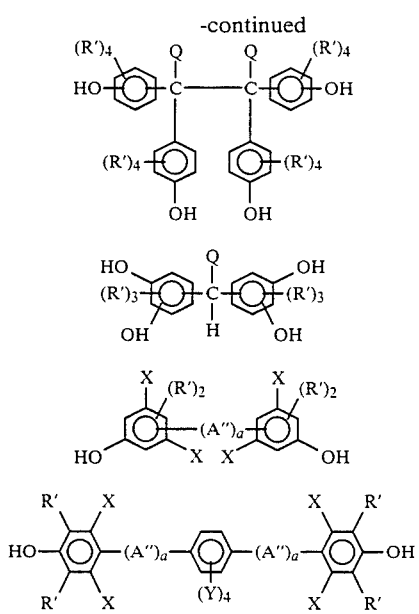

wherein each A is independently a divalent hydrocarbyl group having from 1 to about 12, carbon atoms,

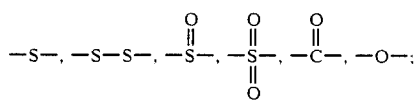

each A' is independently a divalent hydro-carbyl group having from 1 to about 12 carbon atoms; each A" independently is a divalent hydrocarbyl group having from 1 to about 4 carbon atoms; each B is independently represented by the formula

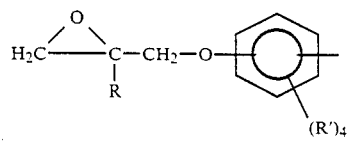

each B' is independently represented by the formula

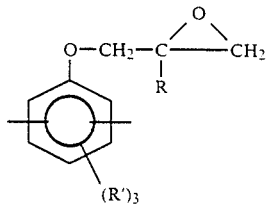

each B" is represented by the formula

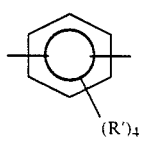

each Q is independently hydrogen or a hydro-carbyl group having from 1 to about 10 carbon atoms; each R is independently hydrogen or an alkyl group having from 1 to about 4 carbon atoms; each R' is independently hydrogen, a hydrocarbyl or hydrocarbyloxy group having from 1 to about 10 carbon atoms or a halogen atom; a has a value of zero or 1; each R" is independently hydrogen, a hydrocarbyl or hydrocarbyloxy group having from about 1 to about 10 carbon atoms, a halogen atom or a glycidyl ether group; each X is independently hydrogen or a halogen atom; each Y independently is hydrogen, a hydrocarbyl or hydrocarbyloxy group having from 1 to about 10 carbon atoms, a halogen atom or a hydroxyl group; each c, c', c" independently has a value from about zero to about 10; m has a value of $n-1$; m' has a value of $n'-1$; m" has a value of $n''-1$; each n, n' and n" independently has a value from zero to about 3; q has a value from zero to about 4; each y independently has an average value from 1 to about 5; y' has an average value of from zero to about 3, each z and z' independently has a value from zero to about 3; and wherein (i) at least one of components (A) and (B) contains at least one halogen atom which is in the meta position with respect to an oxygen atom attached to the ring for each two aromatic rings;

(ii) when the average epoxide functionality of component (A) is not greater than 2 and the average hydroxyl functionality of component (B) is not greater than 2, components (A) and (B) are present in quantities which provide a hydroxyl to epoxide ratio of from about 0.1:1 to about 0.9:1;

(iii) when one of components (A) and (B) has an average functionality of greater than 2 and the other has an average functionality of not greater than 2, components (A) and (B) are present in quantities which provide a hydroxyl to epoxide ratio of from about 0.01:1 to about 0.4:1; and when both components (A) and (B) have an average functionality of greater than 2, components (A) and (B) are present in quantities which provide a hydroxyl to epoxide ratio of from about 0.01:1 to about 0.3:1.

2. A halogen-containing advanced epoxy resin of claim 1 wherein (i) at least one of components (A) and (B) contains at least one halogen atom which is in the meta position with respect to an oxygen atom attached to the ring for each aromatic ring;

(ii) when the average epoxide functionality of component (A) is not greater than 2 and the average hydroxyl functionality of component (B) is not greater than 2, components (A) and (B) are present in quantities which provide a hydroxyl to epoxide ratio of from about 0.2:1 to about 0.7:1;

(iii) when one of components (A) and (B) has an average functionality of greater than 2 and the other has an average functionality of not greater than 2, components (A) and (B) are present in quantities which provide a hydroxyl to epoxide ratio of from about 0.1:1 to about 0.3:1; and (iv) when both components (A) and (B) have an average functionality of greater than 2, components (A) and (B) are present in quantities which provide a hydroxyl to epoxide ratio of from about 0.1:1 to about 0.25:1.

3. A halogen-containing advanced epoxy resin of claim 2 wherein
   (i) at least one of components (A) and (B) contains at least two halogen atoms which are in the meta position with respect to an oxygen atom attached to the ring for each aromatic ring;
   (ii) when the average epoxide functionality of component (A) is not greater than 2 and the average hydroxyl functionality of component (B) is not greater than 2, components (A) and (B) are present in quantities which provide a hydroxyl to epoxide ratio of from about 0.4:1 to about 0.6:1;
   (iii) when one of components (A) and (B) has an average functionality of greater than 2 and the other has an average functionality of not greater than 2, components (A) and (B) are present in quantities which provide a hydroxyl to epoxide ratio of from about 0.15:1 to about 0.25:1; and
   (iv) when both components (A) and (B) have an average functionality of greater than 2, components (A) and (B) are present in quantities which provide a hydroxyl to epoxide ratio of from about 0.15:1 to about 0.2:1.

4. A halogen-containing advanced epoxy resin of claim 3 wherein component (A) is a diglycidyl ether of 2,2',6'6'-tetrabromo-3,3',5,5'-tetramethyl-4,4'-biphen-ol; 2,2',6-tribromo-3,3',5,5'-tetramethyl-4,4'-biphenol; 1,2-bis-(2,6-dibromo-3,5-dimethyl-4-hydroxyphenyl)ethane; bis-(2,6-dibromo-3,5-dimethyl-4-hydroxyphenyl)methane; or a combination thereof.

5. A halogen-containing advanced epoxy resin of claim 4 wherein component (B) is 2,2',6'6'-tetrabromo-3,3',5,5'-tetramethyl-4,4'-biphen-ol; 2,2',6-tribromo-3,3',5,5'-tetramethyl-4,4'-biphenol; 1,2-bis-(2,6-dibromo-3,5-dimethyl-4-hydroxyphenyl)ethane; bis-(2,6-dibromo-3,5-dimethyl-4-hydroxyphenyl)methane; or a combination thereof.

6. A curable composition comprising at least one halogen-containing epoxy resin of claim 1 and a curing quantity of at least one suitable curing agent therefor.

7. A curable composition of claim 6 wherein said curing agent is methylenedianiline, dicyandiamide, diaminodiphenylmethane, sulfanilamide, o-tolylbiguanide, diethylene toluene diamine, phenol-formaldehyde novolac resins, cresol-formaldehyde novolac resins, methylbicyclo[2.2.1]heptene-2,3-dicarboxylic anhydride, ethylene diamine or a combination thereof.

8. A curable composition comprising at least one halogen-containing epoxy resin of claim 2 and a curing quantity of at least one suitable curing agent therefor.

9. A curable composition of claim 8 wherein said curing agent is methylenedianiline, dicyandiamide, diaminodiphenylmethane, sulfanilamide, o-tolylbiguanide, diethylene toluene diamine, phenol-formaldehyde novolac resins, cresol-formaldehyde novolac resins, methylbicyclo[2.2.1]heptene-2,3-dicarboxylic anhydride, ethylene diamine or a combination thereof.

10. A curable composition comprising at least one halogen-containing epoxy resin of claim 3 and a curing quantity of at least one suitable curing agent therefor.

11. A curable composition of claim 10 wherein said curing agent is methylenedianiline, dicyandiamide, diaminodiphenylmethane, sulfanilamide, o-tolylbiguanide, diethylene toluene diamine, phenol-formaldehyde novolac resins, cresol-formaldehyde novolac resins, methylbicyclo[2.2.1]heptene-2,3-dicarboxylic anhydride, ethylene diamine or a combination thereof.

12. A curable composition comprising at least one halogen-containing epoxy resin of claim 4 and a curing quantity of at least one suitable curing agent therefor.

13. A curable composition of claim 12 wherein said curing agent is methylenedianiline, dicyandiamide, diaminodiphenylmethane, sulfanilamide, o-tolylbiguanide, diethylene toluene diamine, phenol-formaldehyde novolac resins, cresol-formaldehyde novolac resins, methylbicyclo[2.2.1]heptene-2,3-dicarboxylic anhydride, ethylene diamine or a combination thereof.

14. A curable composition comprising at least one halogen-containing epoxy resin of claim 5 and a curing quantity of at least one suitable curing agent therefor.

15. A curable composition of claim 14 wherein said curing agent is methylenedianiline, dicyandiamide, diaminodiphenylmethane, sulfanilamide, o-tolylbiguanide, diethylene toluene diamine, phenol-formaldehyde novolac resins, cresol-formaldehyde novolac resins, methylbicyclo[2.2.1]heptene-2,3-dicarboxylic anhydride, ethylene diamine or a combination thereof.

16. The product resulting from subjecting the composition of claim 6 to conditions sufficient to effect curing thereof.

17. The product of claim 16 which is an encapsulated electrical component.

18. The product resulting from subjecting the composition of claim 7 to conditions sufficient to effect curing thereof.

19. The product of claim 18 which is an encapsulated electrical component..

20. The product resulting from subjecting the composition of claim 8 to conditions sufficient to effect curing thereof.

21. The product of claim 20 which is an encapsulated electrical component.

22. The product resulting from subjecting the composition of claim 9 to conditions sufficient to effect curing thereof.

23. The product of claim 22 which is an encapsulated electrical component.

24. The product resulting from subjecting the composition of claim 10 to conditions sufficient to effect curing thereof.

25. The product of claim 24 which is an encapsulated electrical component.

26. The product resulting from subjecting the composition of claim 11 to conditions sufficient to effect curing thereof.

27. The product of claim 26 which is an encapsulated electrical component.

28. The product resulting from subjecting the composition of claim 12 to conditions sufficient to effect curing thereof.

29. The product of claim 28 which is an encapsulated electrical component.

30. The product resulting from subjecting the composition of claim 13 to conditions sufficient to effect curing thereof.

31. The product of claim 30 which is an encapsulated electrical component.

32. The product resulting from subjecting the composition of claim 14 to conditions sufficient to effect curing thereof.

33. The product of claim 32 which is an encapsulated electrical component.

34. The product resulting from subjecting the composition of claim 15 to conditions sufficient to effect curing thereof.

35. The product of claim 34 which is an encapsulated electrical component.

36. An electrical or structural laminate or composite prepared from two or more layers of a substrate impregnated with a composition of claim 6 or a combination of such substrates.

37. An electrical laminate of claim 36 having at least one external layer of an electrically conductive material.

38. An electrical laminate or composite of claim 37 wherein said electrically conductive material is copper.

39. An electrical or structural laminate or composite prepared from two or more layers of a substrate impregnated with a composition of claim 7 or a combination of such substrates.

40. An electrical laminate of claim 39 having at least one external layer of an electrically conductive material.

41. An electrical laminate or composite of claim 40 wherein said electrically conductive material is copper.

42. An electrical or structural laminate or composite prepared from two or more layers of a substrate impregnated with a composition of claim 8 or a combination of such substrates.

43. An electrical laminate of claim 42 having at least one external layer of an electrically conductive material.

44. An electrical laminate or composite of claim 43 wherein said electrically conductive material is copper.

45. An electrical or structural laminate or composite prepared from two or more layers of a substrate impregnated with a composition of claim 9 or a combination of such substrates.

46. An electrical laminate of claim 45 having at least one external layer of an electrically conductive material.

47. An electrical laminate or composite of claim 46 wherein said electrically conductive material is copper.

48. An electrical or structural laminate or composite prepared from two or more layers of a substrate impregnated with a composition of claim 10 or a combination of such substrates.

49. An electrical laminate of claim 48 having at least one external layer of an electrically conductive material.

50. An electrical laminate or composite of claim 49 wherein said electrically conductive material is copper.

51. An electrical or structural laminate or composite prepared from two or more layers of a substrate impregnated with a composition of claim 11 or a combination of such substrates.

52. An electrical laminate of claim 51 having at least one external layer of an electrically conductive material.

53. An electrical laminate or composite of claim 52 wherein said electrically conductive material is copper.

54. An electrical or structural laminate or composite prepared from two or more layers of a substrate impregnated with a composition of claim 12 or a combination of such substrates.

55. An electrical laminate of claim 54 having at least one external layer of an electrically conductive material.

56. An electrical laminate or composite of claim 55 wherein said electrically conductive material is copper.

57. An electrical or structural laminate or composite prepared from two or more layers of a substrate impregnated with a composition of claim 13 or a combination of such substrates.

58. An electrical laminate of claim 57 having at least one external layer of an electrically conductive material.

59. An electrical laminate or composite of claim 58 wherein said electrically conductive material is copper.

60. An electrical or structural laminate or composite prepared from two or more layers of a substrate impregnated with a composition of claim 14 or a combination of such substrates.

61. An electrical laminate of claim 60 having at least one external layer of an electrically conductive material.

62. An electrical laminate or composite of claim 61 wherein said electrically conductive material is copper.

63. An electrical or structural laminate or composite prepared from two or more layers of a substrate impregnated with a composition of claim 15 or a combination of such substrates.

64. An electrical laminate of claim 63 having at least one external layer of an electrically conductive material.

65. An electrical laminate or composite of claim 64 wherein said electrically conductive material is copper.

66. A substrate impregnated with a composition of claim 6.

67. A substrate impregnated with a composition of claim 7.

68. A substrate impregnated with a composition of claim 8.

69. A substrate impregnated with a composition of claim 9.

70. A substrate impregnated with a composition of claim 10.

71. A substrate impregnated with a composition of claim 11.

72. A substrate impregnated with a composition of claim 12.

73. A substrate impregnated with a composition of claim 13.

74. A substrate impregnated with a composition of claim 14.

75. A substrate impregnated with a composition of claim 15.

* * * * *